United States Patent [19]
Brown et al.

[11] Patent Number: 5,376,526
[45] Date of Patent: Dec. 27, 1994

[54] GENOMIC MISMATCH SCANNING

[75] Inventors: Patrick Brown, Stanford; Stanley Nelson, Menlo Park; Sue Klapholz, Stanford, all of Calif.

[73] Assignee: The Board of Trustees of the Leland Stanford Junior University, Stanford, Calif.

[21] Appl. No.: 995,853

[22] Filed: Dec. 23, 1992

Related U.S. Application Data

[63] Continuation-in-part of Ser. No. 880,167, May 6, 1992, abandoned.

[51] Int. Cl.$^5$ .......................... C12Q 1/68; C12P 19/34
[52] U.S. Cl. ........................................ 435/6; 435/91.1; 935/77; 935/78
[58] Field of Search ........................... 435/6, 91.1, 91; 935/77, 78

[56] References Cited

U.S. PATENT DOCUMENTS 5,032,502  7/1991  Stodolsky ............................. 435/6

OTHER PUBLICATIONS

Botstein, D., White R. Skolnick M. & Davis, R. W., *Am J. Hum. Genet*, 32:314-331 (1980).
Donis-Keller H., et al., *Cell* 51:319-337 (1988).
Kidd K. K., et al., *Cytogenet Cell Genet*, 51:662-947 (1989).
Risch, N., *Am. J. Hum. Genet*, 46:242-253 (1990).
Risch, N., *Am J. Hum. Genet*, 46:222-241 (1990).
Lander, E. S. & Botstein, D., *Science*, 236:1567-1570 (1987).
Bishop, D. T. & Williamson, J. A., *Am. J. Hum. Genet*, 46:254-265 (1990).
Lahue, R. S., Au, K. G. & Modrich, P., *Science*, 245:160-164 (1989).
Su, S–S, & Modrich, P., *Proc. Natl. Acad. Sci. USA*, 83:5057-5061 (1986).
Grilley, M., Welsh, K., Su, S–S & Modrich, P., *J. Biol. Chem.*, 264:1000-1004 (1989).
Su, S–S, Grilley, M., Thresher, R., Griffith, J. & Modrich, P., *Genome*, 31:104-111 (1989).
Learn, B. A. & Graftstrom, R. H., *J. Bacteriol.*, 171:6473-6481 (1989).
Sanda, et al., *Nucleic Acids Research*, 14:7265-7284 (1986).
Casna, N. J., Novack, D. F., Hsu, M–T & Ford, J. P., *Nucleic Acids Res.*, 14:7285-7303 (1986).
Cotton, R. G., Rodrigues, N. R. & Campbell, R. D., *Proc. Natl. Acad. Sci. USA*, 85:4397-4401 (1988).
Thomas, D. C., Kinkel, T. A., Casna, N. J., Ford, J. P. & Sancar, A., *J. Biol. Chem.*, 261:14496-14505 (1986).
Myers, R. M., Maniatis, T. & Lerman, L. S., *Methods in Enzymology.*, 155:501-517 (1987).
Henikoiff, S., *Gene*, 28:351-360 (1984).
Sedat, et al., *J. Mol. Biol.*, 26:537-540 (1967).
Iyer, V. N. & Rupp, W. D., *Bioch. Biophys. Acta.*, 228:117-126 (1971).
Lichter, P., Tan, C–JC, Call, K., Hermanson, G., Evans, G. A., Housman, D. & Ward, D. C., *Science*, 247:64-69 (1990).
Pinkel, D., Landegent, J., Collins, C., Fuscoe, J., Seagraves, R., Lucas, J. & Gray, J., *Proc. Natl. Acad. Sci. USA*, 85:9138-9142 (1988).
Lichter, P., Ledbetter, S. A., Ledbetter, D. H. & Ward, D. H., *Proc. Natl. Acad. Sci. USA*, 87:6634-6638 (1990).

*Primary Examiner*—Stephanie W. Zitomer
*Attorney, Agent, or Firm*—Bertram I. Rowland; Pamela J. Sherwood

[57] ABSTRACT

Genetic mapping is provided by combinations of two related general procedures. In the first procedure, mapping is provided by identifying genetic regions from which DNA fragments derived from two individuals can combine to form extensive hybrids free of base mismatches. DNA is processed by a method that allows perfectly-matched hybrid DNA molecules formed between DNAs from the two individuals, to be separated from imperfectly-paired DNA hybrids or hybrids in which both strands are from the same individual's DNA. The perfectly-matched hybrid DNAs can then be labeled and the labeled DNA used as probes to identify loci of identity-by-descent between the two individuals. In the second procedure, nicks are introduced specifically into DNA hybrids formed between non-identical alleles from a region of heterozygosity in an individual diploid genome. The nicked DNA molecules are then specifically labeled to provide probes for identifying regions of heterozygosity in the genome of an individual.

10 Claims, No Drawings

GENOMIC MISMATCH SCANNING

CROSS-REFERENCE TO GOVERNMENT GRANT

This invention was made with Government support under contract HG00450 awarded by the National Institutes of Health. The government may have certain rights in this invention.

CROSS-REFERENCE TO RELATED APPLICATIONS

This application is a continuation-in-part of application Ser. No. 880,167 filed on May 6, 1992 now abandoned.

INTRODUCTION

1. Technical Field

The field of this invention is genetic mapping.

2. Background

Linkage mapping of genes involved in disease susceptibility and other traits in humans, animals and plants has in recent years become one of the most important engines of progress in biology and medicine. The development of polymorphic DNA markers as landmarks for linkage mapping has been a major factor in this advance. However, current methods that rely on these markers for linkage mapping in humans are laborious, allowing screening of only at most a few markers at a time. Furthermore, their power is limited by the sparsity of highly-informative markers in many parts of the human genome.

To map genes whose manifestations are recognized only in the whole organism, the standard approach relies on identifying linkage between the trait and a genetic marker whose map position is already known. The most abundant and generally useful class of markers in the human genome are DNA sequence polymorphism either restriction fragment length polymorphisms (RFLP's) or other DNA polymorphisms that can be detected by hybridization with specific probes or by amplification using specific primers.

RFLP mapping and related methods have had dramatic successes. However, their utility is limited by two problems: First, many discrete loci need to be examined, but only one or a few loci can be typed at a time, which procedure is arduous; second, the low density on the map and low polymorphism information content (PIC value) of available markers means that multiple members of each family need to be typed to obtain useful linkage information, even when only two share the trait of interest. While these disadvantages can be overcome to some degree by automation and technical improvements, as well as by developing closely-spaced extremely polymorphic markers, the use of discrete markers for specific map intervals has inherent limitations. The limitations are particularly marked when applied to mapping strategies that seek to reduce the number of individuals that need to be analyzed in each family.

It is generally much easier to collect many pairs of related individuals who share a trait of interest than to collect a few large, well-documented pedigrees in which the trait is segregating. In the former case, the absolute number of individuals is smaller. For medically-significant traits, affected individuals are likely to present themselves for examination, whereas other family members need to be traced and recruited. Furthermore, individuals vital to pedigree analysis may be deceased. Yet the low density and low information content of available markers makes the use of pedigrees almost mandatory for linkage mapping by RFLP analysis. Collection of appropriate families frequently poses the principal barrier to mapping genes that influence human traits, particularly genetically complex traits. Strategies have been reported for linkage mapping using the information in DNA from multiple very small sets of affected relatives (typically pairs or even single individuals). However, these strategies depend upon the availability of closely-spaced highly information genetic markers throughout the genetic map.

The issues raised above in reference to linkage mapping also apply to genetic risk assessment in medicine.

In principle, any base that differs among allelic sequences could serve as a marker for linkage analysis. Single-base differences between allelic single copy sequences from two different haploid genomes have been estimated to occur about once per 300 bp in an outbred Western European population. This calculates to a total of about $10^7$ potential markers for linkage analysis per haploid genome. Only a tiny fraction of these nucleotide differences contribute to mapping using current methods. There is, therefore, substantial interest in developing new methods that utilize the available genomic information more efficiently and can provide information concerning multi-gene traits. Such methods could be valuable, not only for gene mapping, but also for genetic diagnosis and risk assessment.

RELEVANT LITERATURE

Articles describing the use of RFLP's are described in Botstein, et al., (1980) *Am. J. Hum. Genet.* 32:314–331; Donis-Keller, et al. (1988) *Cell* 51:319–337; Kidd, et al. (1989) *Cytogenet. Cell. Genet.* 51:622–947 and Risch (1990) *Am. J. Hum. Genet.* 46:242–253. Mapping strategies may be found in Risch (1990) *Am. J. Hum. Genet.* 46:229–241; Lander and Botstein (1987) *Science* 36:1567–1570; and Bishop and Williamson (1990) *Am. J. Hum. Genet.* 46:254–265. Sandra and Ford, (1986) *Nucleic Acids Res.* 14:7265–7282 and Casna, et al. (1986) Nucleic Acids Res. 14:7285–7303 describe genomic analysis.

SUMMARY OF THE INVENTION

Genomic analysis is achieved through the process of: Digesting DNA to be compared from two different sources, usually individuals who are genetically related or suspected of being genetically related, with a restriction enzyme that cuts relatively infrequently; combining single strands of the genomic fragments from the two individuals under conditions whereby heterohybrids (hybrids containing one strand from each individual) can be distinguished from homohybrids (hybrids containing both strands from the same individual); separating homohybrids from heterohybrids; separating mismatch-free heterohybrids from hybrids with mismatches; preparing labeled probes from the mismatch-free heterohybrids; and identifying regions of genetic identity between the two individuals by means of said labeled probes. The mismatch-free heterohybrids provide highly specific probes for regions of genetic identity by descent, since sufficiently large hybrid DNA molecules formed from non-identical regions are expected to have at least one and usually many base mismatches.

Alternatively, one may map regions of heterozygosity, and, by inference, homozygosity in a single individual by isolating DNA fragments substantially free of multicopy DNA; melting the DNA and reannealing to provide for hybrid fragments; introducing nicks specifically in mismatched DNA; labeling the nicked DNA; and using the labeled DNA as probes to identify regions of heterozygosity. Regions of homozygosity or hemizygosity (where all or a significant portion of a chromosome is missing, e.g. aneuploidy) are inferred by the absence of hybridized label.

DESCRIPTION OF THE SPECIFIC EMBODIMENTS

Methods and compositions are provided for genomic mapping by identifying regions of the genome at which DNA sequences from two DNA sources are perfectly identical over long stretches (typically $10^3$ to $2\times10^4$ nt). Depending upon the nature of the probe, the procedures may vary. In a procedure that allows for labeling of regions of genetic identity between two individuals, DNA sources are digested with a restriction enzyme that cuts infrequently; the resulting DNA is processed to isolate mismatch-free heterohybrid dsDNA fragments free from mismatch containing or homohybrid fragments; the mismatch-free heterohybrid fragments are labeled and then used to identify regions of genetic identity between the two sources.

Alternatively, to map regions of homozygosity or heterozygosity in an individual genome, one may digest the DNA from that individual; optionally, remove multi-copy DNA; melt and reanneal the DNA; introduce nicks into mismatched dsDNA; label the mismatched dsDNA; and use the labeled DNA as probes for identifying genomic regions that are heterozygous, leaving regions that are homozygous or hemizygous having substantially lower labeling.

The DNA source may be any source, haploid to polyploid genomes, normally eukaryotic, and may include vertebrates and invertebrates, including plants and animals, particularly mammals, e.g. humans. The DNA will be of high complexity where each of the sources will usually have greater than $5\times10^4$ bp, usually greater than $10^6$ bp, more usually greater than about $10^7$ bp. Thus, in any situation where one wishes to compare two sources of DNA as to their genetic similarities, whether the sources are related or not, the subject method may be employed. Usually, the sources will be related, being of the same species, and may be more closely related in having a common ancestor not further away than six, frequently four, generations.

For linkage mapping or genetic diagnosis, genetically related individuals are required. Thus, the subject method may find application in following segregation of traits associated with breeding of plants and animals, the association of particular regions in the genomic map with particular traits, especially traits associated with multiple genes, the transmission of traits from ancestors or parents to progeny, the interaction of genes from different loci as related to a particular trait, and the like. While only two sources may be involved in the comparison, a much larger sampling may be involved, such as 20 or more sources, where pairwise comparisons may be made between the various sources. Relationships between the various sources may vary widely, e.g. grandparents and grandchildren; siblings; cousins; and the like.

Depending upon whether the regions of genetic identity or regions of non-identity are to be labeled, the treatment of the DNA from the source will vary. The DNA may be processed initially in accordance with conventional ways, lysing cells, removing cellular debris, separating the DNA from proteins, lipids or other components present in the mixture and then using the isolated DNA for restriction enzyme digestion. See Molecular Cloning, A Laboratory Manual, 2nd ed. (eds. Sambrook et al.) CSH Laboratory Press, Cold Spring Harbor, N.Y. 1989. Usually, at least about 0.5 μg of DNA will be employed, more usually at least about 5 μg of DNA, while less than 50 μg of DNA will usually be sufficient.

The following procedure will address solely the methodology employed for isolating and labeling of DNA corresponding to regions of identity-by-descent between two related individuals. The total DNA from both cellular sources is digested completely with a restriction enzyme that cuts relatively infrequently, generally providing fragments of strands of about $0.2-10\times10^4$ nt, preferably of about $0.5-2\times10^4$ nt. The size is selected to substantially ensure the presence of at least one GATC sequence, and at least one base difference between any allelic fragments not identical by descent i.e. to ensure that homohybrid fragments, or heterohybrid fragments that are not identical by descent, sustain at least one cut in a subsequent step. This enzyme will normally recognize at least a 6-nucleotide consensus sequence and may involve either blunt-ended or staggered-ended cuts. For the method described in detail here, an enzyme that cuts to leave a protruding 3' end is needed. The protruding 3' ends are preferred specifically when exonuclease III digestion, followed by benzoylated naphthlated diethylaminoethyl cellulose BNDC binding, is ultimately used to eliminate homohybrids and mismatched DNA's. Restriction enzymes yielding other sorts of ends may be preferred if other specific steps are substituted, as described further below.

The resulting DNA fragments are then processed to provide for a means of separating complementary DNA hybrids, where the two strands are from different sources, from complementary DNA hybrids where the two strands are from the same source. This may be achieved in different ways. The method exemplified in the subject invention uses the following steps. DNA from one of the sources is methylated with a sequence specific methylase, such as Dam methylase or a restriction methylase, so as to substantially completely methylate the consensus sequences of the DNA from one of the sources. The other source is left unmodified or methylated completely with a different restriction methylase.

The two DNA samples are then mixed, denatured and allowed to reanneal. A practical rate of complete annealing of the complex DNA samples can be achieved by using chemical or protein catalysts under conditions that preserve large DNA strands (Casna, et al. (1986) *Nucleic Acids Res.* 14:7285-7303; Barr and Emanuel (1990) *Anal. Bioch.* 186:369-373; Anasino (1986) ibid 152:304-307). It is also necessary to avoid or minimize network formation resulting from rapid hybridization of non-allelic repeated sequences, so that simple fully-duplex products can be recovered even when dispersed repetitive sequences are embedded in them. Annealing conditions that have been shown to meet this requirement are FPERT conditions as described in Casna (1986) supra.

The reannealed DNA mixture is digested with two methylation-sensitive restriction endonucleases. Hybrids formed between the two different DNA specimens will be hemimethylated at the methylation sites. The restriction enzymes are selected so as to digest sites which are unmethylated or doubly methylated, while being incapable of cleaving the hemimethylated sites. Desirably, the sequence will be a relatively common sequence, generally occurring on the average of about $1-10 \times 10^2$, preferably about $1-5 \times 10^2$. A more stringent selection for mixed-donor hybrids can be achieved by using additional combinations of restriction/modification enzymes (Casna (1986) supra). Optionally, one may remove unannealed DNA (single stranded DNA) at this time using any convenient method, e.g. adsorbtion to BNDC.

Various combinations of enzymes can be employed. The combination should ensure that there is at least one cut in any homohybrid fragment, preferably at least two or more, so the sequence should be relatively common. For example, E. coli dam methylase, which recognizes GATC for methylation, may be employed for methylation. This modification enzyme may then be used with the methylation-sensitive restriction endonucleases DpnI and MboI, which cleave at GATC sites, the former at doubly-methylated sites and the latter at unmethylated sites. The particular sequence "GATC" is found every few hundred bp in the human genome. While a single restriction/modification site is preferable, two or three sites may be involved where different combinations of modification and restriction enzymes are employed. With DNA from sources other than human, other combinations of modification enzymes and restriction enzymes may be employed.

Alternative procedures for modifications are as follows. By cutting the two DNA samples using a different restriction enzyme for each specifically two enzymes that share a common recognition sequence but in one case cut with an N-base 3' overhang, and in the other with an N-base 5' overhang-only the heterohybrids will have flush ends. An example of such a pair of restriction enzymes for the case N=4, is Acc65I and KpnI. The hybrids with both strands derived from the same DNA sample will retain either a 5' or 3' overhanging end.

The flush-ended heterohybrids will uniquely be able to be ligated to a flush-ended partner, such as an oligonucleotide. This oligonucleotide might, for example, have a hairpin structure, such that the "capped" ends are protected from exonuclease digestion. Variations on this principle are possible, exploiting the distinctive structures of the ends of heterohybrids compared with homohybrids, when related restriction enzyme pairs are used.

This strategy for selecting heterohybrids can replace the MboI/DpnI digestion step in selecting heterohybrids. However, a 5' to 3' exonuclease, such as bacteriophage lambda exonuclease, or a combination of a helicase and exonuclease VII and/or I, or another combination of enzymes to allow digestion of all uncapped ends would need to be used in addition to, or in place of exonuclease III, following the MutHLS nicking step in the procedure outlined below.

Other techniques may also be used for the initial separation of homohybrids from heterohybrids. By growing the cells from one of the sources with heavy isotope-labeled nucleosides, heavy atom labeled nucleosides, or other isotope labeled precursors, the two strands from the different sources will differ in density. Isotopes that may be used include $^{15}N$, $^{13}C$, $^{2}H$, etc. The duplexes may then be separated by density banding.

Alternatively, one may label the DNA from the two sources with different labels, e.g. using labeled nucleotides and terminal deoxynucleotidyl transferase, by random conjugation, and the like. One can then separate all of the duplexes as to one label, and then divide that group into homo- and heterolabeled duplexes. For example, biotin and avidin may be used to separate at one stage, where the avidin is bound to magnetic beads, and 2,4-dinitrophenyl and anti-(2,4-dinitrophenyl) may then be used for the second separation, where the anti-(2,4-dinitrophenyl) is bound to a support.

Alternatively, one may select restriction enzymes which provide for overhangs, where heterohybrids will result in blunt ends or overhangs that differ from those of the homohybrids. One may then use the overhangs to separate homohybrids leaving the heterohybrids.

Returning to the description of a principal embodiment, the resulting mixture of uncut heterohybrids, and MboI or DpnI cut homohybrids is then subjected to a system which allows for separation of DNA duplexes with some mismatched base pairs from complementary perfectly-matched DNA duplexes. See, for example, Lahue, et al. (1989) Science 245:160–164; Su and Modrich (1986) Proc. Natl. Acad. Sci. USA 83:5057–5061; Grilley, et al. (1989) J. Biol. Chem. 264:1000–1004; Su, et al. (1989) Genome 31:104–111; and Learn and Grafstrom (1989) J. Bacteriol. 171:6473–6481.

Illustrative of such a system is the "methyl-directed mismatch repair" pathway of E. coli. The system uses the purified mutS, mutL, mutH and uvrD gene products, as well as exonuclease I, exonuclease VII or RecJ exonuclease, single strand binding (SSB) protein and DNA polymerase III. In vitro, seven of the eight possible single base mismatches, as well as small insertions and deletions are efficiently recognized. When DNA synthesis is prevented, the system specifically introduces large gaps in the mismatch-containing molecules. The purified mutS, mutL and mutH proteins act in concert to introduce nicks specifically into DNA molecules that contain base mismatches. With the exception of C—C mismatch, the other mismatches are effectively identified by one or more of the MutX enzymes (X indicates S, L or H).

Exonuclease III can initiate exonucleolytic digestion at a nick and digest the nicked strand in the 3' to 5' direction to produce a region, e.g. a gap. Exonuclease III can also initiate digestion at a recessed or flush 3' end, but it cannot initiate digestion at a protruding 3' end of a linear duplex. Digestion from the ends of the linear DNA hybrids can, therefore, be prevented by choosing a restriction enzyme that produces protruding 3' ends for the initial digestion of the genomic DNA (Henikoff (1984) Gene 28:351–360). The DNA ends produced by the restriction enzymes used to make the smaller fragments for distinguishing hemimethylated sites from unmethylated or dimethylated sites are selected to provide recessed (e.g. MboI) or flush (DpnI) 3' termini and these termini are susceptible to digestion by exonuclease III. Therefore, exonuclease III provides for partial single strands in hybrid molecules where both strands are derived from the same individual or where the strands contain base mismatches.

In carrying out the process, the duplexes obtained from annealing and restriction digestion are exposed to the methyl-directed mismatched repair system in vitro. The mutS, mutL and mutH introduce nicks specifically into the mismatched DNA molecules, while the exonuclease III can introduce gaps at nicked sites and at recessed 3' termini. The mismatch-free heterohybrids, corresponding to regions of identity-by-descent between the sources, can now be distinguished from all other duplexes by virtue of the absence of significant gaps or partial single strand regions.

The partially single stranded and single stranded DNA is now separated from the fully-duplex DNA. This can be efficiently achieved using benzoylated naphthylated DEAE cellulose (BNDC). At high salt concentration, BNDC retains single stranded and partially single-stranded DNA molecules with high efficiency and may be separated by centrifugation or other separation means. The unbound DNA molecules are recovered, which in this case comprise complementary sequences from the two sources.

A more complete methyl-directed mismatch repair enzyme system may ultimately prove to be superior in specificity to the simple system using only MutS, MutL and MutH. For example, MutL, MutS and MutH, plus helicase II (UvrD protein), exonuclease I, exonuclease VII, single-strand binding protein, and DNA polymerase III, acting in concert, can carry out mismatch dependent DNA synthesis, and thereby specifically introduce labeled or modified nucleotides into mismatch-containing DNA molecules. For example, by using biotinylated nucleotides, mismatched DNA molecules can be specifically biotinylated, and then immobilized avidin or related methods can be used to remove the mismatched molecules from a mixture of perfectly-matched and mismatched DNA molecules. Alternatively, use of the same set of enzymes, excluding DNA polymerase, would lead directly to gaps in the mismatched DNA eliminating the exonuclease III step. For such a procedure, the ends of the linear DNA molecules produced in the initial annealing step would need to be protected from the action of the exonucleases and helicase. This procedure would thus interface well with the end-capping method suggested above as an alternative method for selection for heterohybrid molecules.

It is fairly obvious that related enzyme systems based on mismatch repair protein from *E. coli* or other organisms could in principle substitute here for the particular enzyme system described.

The mismatch-free heterohybrid dsDNA duplexes may be used without expansion. The subject method provides a sufficiently clean separation of the mismatch-free heterohybrid dsDNA duplexes in sufficient amount to allow for their labeling and direct use as probes. By using a readily available amount of DNA which can be efficiently handled, generally from about 0.5 to 100 $\mu g$ DNA, usually about 1 to 10 $\mu g$ DNA, from each source, a satisfactory amount of the mismatch-free heterohybrid dsDNA duplexes are obtained for labeling and probing a DNA sample.

The mismatch-free heterohybrid dsDNA sequences from the two sources can be used for identifying the regions of identity-by-descent between the two sources. Conveniently, the dsDNA may be labeled for use as a probe to identify the corresponding genomic regions. A wide variety of labels may be employed, particularly radio-isotopes, fluorescers, enzymes, and the like. The particular choice of label will depend upon the desired sensitivity, the nature of the genomic sample being probed, the sensitivity of detection required, and the like. Thus, the more complex the genome under analysis, the higher the sensitivity which would be desired. Various instruments are available which allow for detection of radioactivity, fluorescence, and the like.

The probes may be prepared by any convenient methodology, such as nick translation, random hexamer primed labeling, polymerase chain reaction using primers that prime outward from dispersed repetitive sequences or random sequences, and the like.

The DNA that is probed may take a variety of forms, but essentially consists of a physically-ordered array of DNA sequences that can be related back to the physical arrangement of the corresponding sequences in the genome (See Boyle, et al. (1990) *Genomics* 7:127–130; Penkel, et al. (1988) *PNAS USA* 87:6634–6638). A metaphase chromosome spread is one naturally-occurring example of such an array. Alternatively, and preferably, a partial or a complete collection of cloned, amplified, or synthetic DNA sequences corresponding to known genetic locations, immobilized in an ordered array on a solid substrate such as a membrane or a silicon or plastic chip, can be used as the target for probing.

The hybridizations with the probes are performed under conditions that allow the use of complex mixtures of DNA probes and suppress artifactual hybridization to repeated sequences (Boyle, et al. (1990) *Genomics* 7:127–133; Pinkel, et al. (1988) *Proc. Natl. Acad. Sci. USA* 85:9138–9142; Lichter, et al. (1990) ibid 87:6634–6638). For example, in the case of grandparent-grandchild pairs, hybridization should occur in approximately 25 large patches (averaging about $4\mu$ in length when prometaphase chromosomes are used), which in aggregate should cover about one-half of the genome.

The boundaries of the patches will be determined by the ends of chromosomes and sites of meiotic crossing over. The boundaries will reflect sites of meiotic recombination that occurred in meioses intervening between the two relatives. Since the areas of hybridization will typically be in large contiguous patches, the method is very robust with respect to contamination of the probe with sequences representing regions that are not identical between the two subjects. Even if only a modest enrichment of identical-by-descent sequences is achieved, the patches of identity and non-identity should be distinguishable as contiguous blocks of greater or lower signal intensity.

Alternatively, rather than using the selected mismatch-free, heterohybrid restriction fragments as probes, they themselves can be immobilized on a solid substrate, typically a Southern blot performed after resolving the DNA restriction fragments by gel electrophoresis. The immobilized fragments can then be probed by hybridization using labelled DNA probes specific to regions of interest. The presence or absence of hybridizing bands recovered from a specific pairwise comparison will indicate whether the pair has identity by descent at the locus in question. This procedure is likely to be useful for refining the resolution of a map, after initial mapping is achieved by using selected fragments as probes.

Genetic regions identified by this mapping method may be cloned by standard methods or in some cases by direct cloning of the sequences selected by genomic mismatch scanning. These sequences can then be analyzed for their biological function, and in some cases used directly or in synthetic or modified form for diagnostic or therapeutic applications.

When the region of genetic identity between two or more individuals is sufficiently small, for example, in plant breeding when products of serial backcrosses with selection for a useful trait are compared, it may be useful to clone the selected identical-by-descent restriction fragments, since the resulting clone pool would be highly enriched for the desired gene sequence (responsible for the selected trait).

An alternate embodiment of genetic mapping looks to differences within an individual genome. One may look to identify regions of a genetic map where an individual or a sample is or is not heterozygous. This method is predicated on the isolation of single-copy sequences corresponding to regions of heterozygosity in the test individual, based on the ability of that individual's DNA to give rise to hybrid DNA molecules with base mismatches when the individual's DNA is denatured and reannealed. The selected mismatched hybrid sequences are then labeled and used as probes for hybridization to a physically ordered array of a genomic DNA sample. Because regions of the genome that lack heterozygosity are unable to produce single-copy DNA hybrids with base mismatches, these regions are visualized as gaps in the hybridization pattern. The following is an exemplary protocol.

The DNA sample is digested to completion with a restriction enzyme that cuts the DNA frequently enough that most of the resulting fragments should not contain repetitive sequences. Illustrative restriction enzymes include enzymes having four nucleotide consensus sequences, such as AluI, RsaI, TaqI, HaeIII and MboI. The resulting fragments will for the most part be in the range of about 200–4000 nucleotides. After melting or denaturing the DNA, the DNA is allowed to reanneal in solution, where the rapidly reannealing multi-copy or repeated DNA sequences (low $C_0t$) are removed, for example, by hydroxyapatite chromatography, based on their rapid reannealing, followed by allowing the remaining DNA to anneal completely. Removal of the low $C_0t$ number DNA is desirable, but may not be essential. After complete reannealing, desirably removing residual unannealed DNA, the small, mostly single-copy DNA fragments that remain are incubated with the methyl-directed mismatch repair proteins described above and ATP to produce nicks in mismatched DNA duplexes. The nicks introduced specifically in mismatched molecules by the methyl-directed mismatch repair allow for nick-translation DNA synthesis by the DNA polymerase, and thus allow labeling with radiolabeled or other labled nucleotide triphosphates. A polymerase that lacks 3' to 5' exonuclease activity, but retains 5' to 3' exonuclease activity, e.g. Taq polymerase, is preferred for this step to avoid labeling by replacement synthesis at the ends of the fragments.

The described procedure will provide probes that densely and specifically cover the regions of the genetic map that are heterozygous in the test individual. Conversely, the regions that are not heterozygous will not provide labeled probes and so should be recognized as distinctive gaps in the hybridization signal. In general, except where the coefficient of inbreeding is very low, the regions of homozygosity will be in contiguous patches of sufficient size, that even a few, e.g. 3–10-fold difference in hybridization intensity between homozygous and heterozygous sites should produce discernible boundaries. Thus, as indicated previously, the separation of heterozygous from homozygous sequences need not be absolute. In addition to clinical and mapping applications, this procedure is likely to be useful in plant and animal breeding, since backcrossing and selection can be used to isolate a gene responsible for a trait of interest to a small region of heterozygosity or homozygosity.

For convenience, kits may be supplied which provide the necessary reagents in a convenient form and together. For example, for the genomic mismatch screening, kits could be provided which would include at least two of the following: The restriction enzymes: one or more which provide for average fragments from the target genome of a size in the range of about $0.5-10 \times 10^4$; one or more modification enzymes; and restriction enzymes which distinguish between hemimethylation and unmethylated or dimethylated consensus sequences; enzymes capable of introducing nicks at mismatches and expanding the nick to a gap of many ($\geq 10$) nucleotides; DNA polymerase; BNDC cellulose; and labeled triphosphates or labeled linkers for blunt end ligation or other composition for labeling the sequences to provide probes. Other components such as a physically ordered array of immobilized DNA genomic clones or metaphase chromosomes, automated systems for determining and interpreting the hybridization results, software for analyzing the data, or other aids may also be included depending upon the particular protocol which is to be employed.

The subject methodology may find particular application in mapping genes by use of affected relative pairs—that is, pairs of relatives that have a genetically influenced trait of interest. "Affected relative pair" methods are preferred, particularly when the penetrance of the allele that confers the trait is low or age-dependent, or when the trait is multigenic or quantitative, e.g. height and build. Disease-susceptibility genes are particularly relevant. By determining where on the genetic map a small set, including two, of "affected" relatives have inherited identical sequences from a common source, and disregarding other family members, a highly efficient strategy for extracting linkage information from a pedigree is provided. The resulting identity-by-descent maps from multiple pairs of similarly-affected relatives can be combined and the composite map searched for loci where genotypic concordance between affected relatives occurs more frequently than would be expected by chance. With a sufficiently large number of affected relative pairs, such an analysis can reveal the positions of genes that contribute even a slight susceptibility to the trait. The procedure may also find wide application in routine screening for shared genetic risks in families.

The following examples are offered by way of illustration and not by way of limitation.

EXPERIMENTAL

*Saccharomyces cereviseae*, Baker's yeast, was used as a test system, because this is genetically the best characterised eukaryotic organism, and it is easy to prepare and characterize yeast clones of defined genetic relatedness.

Test of the method: Two independently isolated haploid clones of Saccharomyces, Y55 (HO his4 leu2 CAN1$^S$ ura3 GAL2) and Y24 (ho HIS4 LEU2 MATa can1$^R$ URA3 GAL2), both derivatives of common lab strains, were used for the experiment. We estimate from RFLP analysis that Y55 and Y24 (a derivative of S288C) differ at approximately one base pair per 100.

The two strains were mated, and the resulting diploid hybrid was sporulated, yielding 4 haploid spore clones. For any given gentic locus, each spore clone ("daughter") received either the Y55 or the Y24 allele. The purpose of the test was to determine if we could specifically isolate, en masse, DNA from all the loci at which two individuals (here, pairs of parent and daughter clones) share genetic identity, excluding DNA from all regions where there was no identity by descent between the pair. We applied our genome mismatch scanning method to determine for several loci, which spore clones had identity by descent with each parent. The results of the genome mismatch scanning analysis were compared with results from conventional analysis (Table 1), using auxotrophic and drug resistance markers. Conventional analysis consisted of testing for growth on appropriate selective media. Four loci were tested-HIS4, CAN1, URA3, GAL2. HIS 4 is on chromosome 3, CAN1 and URA3 on chromosome 5, and GAL2 is on chromosome 12. Our analysis of these loci included a total of 15 independent PstI restriction fragments, each of which constituted an independent test of the genomic mismatch scanning method, as their sometimes adjacent location in the genome was immaterial to their behaviour in the selection. The result of the test was that all 15 PstI restriction fragments analyzed were recovered if and only if they were identical by descent between the parent and daughter being compared (Tables 1 and 2). This result confirms the principles underlying genomic mismatch scanning.

Procedure

1. DNA Isolation: High molecular weight DNA was isolated from each yeast strain (parent or spore clone) by a standard method (*Methods in Enzymology* 194 (chapter 11):169-182).

2. Initial Restriction Enzyme Digestion: Each DNA sample was digested completely with PstI restriction enzyme. The DNA was recovered by phenol:chloroform extraction, and ethanol precipitation, and resuspended in Tris-HCl 10 mM EDTA 1 mM, pH 8.0.

3. Methylation of DNA From Parental Strains with Dam Methylase: DNA samples from the two parental strains, Y55 and Y24, were fully methylated with *E. coli* Dam methylase (New England Biolabs), at a DNA concentration of 0.25 mg/ml, using 4 units of enzyme/µg of DNA in an overnight incubation at 37°, in the buffer recommended by the manufacturer. The samples were extracted with phenol:chloroform, ethanol precipitated, and resuspended in Tris-HCl 10 mM, EDTA 1 mM, pH 8.0.

4. Mixing and Solution Hybridization of Paired Test DNA Samples

A. Y55 DNA (5 µg in 45 µl)+spore clone 1 b DNA (5 µg in 80 µl) was denatured by adding 7.5 µl of 5M NaOH. After 10 min at room temperature, the sample was neutralized by adding 16 µl of 3M MOPS acid. 32 µl of formamide and 200 µl of 2X PERT buffer (4M NaSCN 20 mM Tris-HCl pH 7.9, 0.2 mM EDTA) were then added, and the sample was adjusted to 400 µl with water. 90% phenol in water was added until an emulsion was apparent (about 80 µl), and then the sample was agitated to maintain the emulsion for 12 hours at room temperature (typically about 23°).

B. Y55 DNA (5 µg in 45 µl)+spore clone 1c DNA (5 µg in 45 µl) was denatured by adding 5.4 µl of 5M NaOH. After 10 min at room temperature, the sample was neutralized by adding 12 µl of 3M MOPS acid. 32 µl of formamide and 200 µl of 2X PERT buffer were then added, and the sample was adjusted to 400 µl with water. 90% phenol in water was added until an emulsion was apparent (about 150 µl), and then the sample was agitated to maintain the emulsion for 12 hours at room temperature (typically about 23°).

C. Y24 DNA (5 µg in 45 µl)+spore clone 1a DNA (5 µg in 45 µl) was denatured by adding 5.4 µl of 5M NaOH. After 10 min at room temperature, the sample was neutralized by adding 12 µl of 3M MOPS acid. 32 µl of formamide and 200 µl of 2X PERT buffer were then added, and the sample was adjusted to 400 µl with water. 90% phenol in water was added until an emulsion was apparent (about 150 µl), and then the sample was agitated to maintain the emulsion for 12 hours at room temperature (typically about 23°).

D. Y24 DNA (5 µg in 45 µl)+spore clone 1c DNA (5 µg in 45 µl) was denatured by adding 5.4 µl of 5M NaOH. After 10 min at room temperature, the sample was neutralized by adding 12 µl of 3M MOPS acid. 32 µl of formamide and 200 µl of 2X PERT buffer were then added, and the sample was adjusted to 400 µl with water. 90% phenol in water was added until an emulsion was apparent (about 150 µl), and then the sample was agitated to maintain the emulsion for 12 hours at room temperature (typically about 23°).

To recover DNA, the samples were each extracted once with choloroform, then ethanol precipitated, and resuspended in 200 µl of Tris/EDTA.

5. Digestion of Homohybrid Molecules (Both Strands From the Same Source) with DpnI+ and MboI+: 105 µl of each of the homohybrid strands was digested at 37° for 2 hours in a final volume of 400 µl of NEB buffer 3 with 100 units of DpnI and and 25 units of MboI.

6. Removal of Residual Unannealed DNA: After MboI/DpnI digestion, samples were extracted with phenol/chloroform, 100 µl of 5M NaCl was added to each and then samples were incubated with 100 mg of BNDC cellulose (Sigma) equilibrated with 50 µM tris, pH 8.0, 1M NaCl, at 4° for 3 hours. The sample was centrifuged at 14000 rpm in a microfuge, then the supernatant was extracted twice with phenol/chloroform and once with choroform, then ethanol precipitated, washed with 70% ethanol, dried and resuspended in 90 µl of Tris-HCl 10 mM EDTA 1 mM, pH 8.0.

7. Selective nicking of mismatched hybrid DNA's: 15 µl of each DNA sample was mixed with 5.2 ng of MutH protein, 340 ng of MutL protein, 700 ng of MutS protein (all proteins provided in purified form by Paul Modrich, Duke University), in a final volume of 60 µl of a buffer consisting of: 50 mM Hepes (pH 8.0), 20 mM KCl, 5 mM MgCl$_2$, 1 mM DTT, 50 µg/ml bovine serum albumin, and 2 mM ATP. The mixture was incubated at 37° for 30 minutes, and the reaction was then stopped by heating to 65° for 10 minutes.

8. Exonuclease III Digestion to Convert Nicks into Single-Strand Gaps, and Ends from MboI or DpnI Cleavage into Single-Strand Tails: The volume of the entire sample from step 7 was adjusted to 200 µl by adding 140 µl of a buffer consisting of: 50 mMTris-HCl (pH 8.0), 5 mM MgCl$_2$, 10 mM β-mercaptoethanol. Then 10 units of exonuclease III were added and incubation continued for 10 min at 37°. This reaction was stopped by adding EDTA to 10 mM, followed by extraction with phenol/chloroform.

9. Removal of Partially or Fully Single-Stranded DNA Molecules from the Mixture: 50 µl of 5M NaCl+250 µl of 1M NaCl were added to adjust to a volume of 500 µl at a concentration of 1M NaCl. 100 mg of BNDC cellulose equilibrated with 50 mM tris, pH 8.0, 1M NaCl, was added and the mixture incubated at 4° for 3 hours. (Sedert, et al. (1967) *J. Mol. Biol.* 26:537–540; Iyer and Rupp (1971) *Bioch. Biophys. Acta.* 228:117–126) The mixture was centrifuged at 14000 rpm for 1 min, then the supernatant was extracted once with phenol/chloroform, and ethanol precipitated overnight. The small pellets were resuspended in 15 μl of Tris-HCl 10 mM, EDTA 1 mM, pH 8.0.

10. Analysis of the Selected DNA pool by Southern Blotting: One-sixth of each of the resulting DNA samples were electrophoresed through a 0.7% agarose gel, in TBE buffer for 15 hours at 70 volts. DNA was transferred to a nylon filter by Southern blotting, and the filter was probed successively with labelled DNA from lambda phage clones corresponding to the 4 specific genetic loci, HIS4, CAN1, URA3 AND GAL2. In each case, 3–5 restriction fragments were readily detected in the lanes corresponding to DNA samples that had identity by descent at the test loci, and not in the lanes corresponding to samples that were known from direct tests not to match at the locus being probed (see Table 1 and 2).

TABLE 1

| Strain | | Locus | | | |
|---|---|---|---|---|---|
| | | CAN1 | URA3 | HIS4 | GAL2 |
| parents | Y24 | A | A | A | A |
| | Y55 | B | B | B | B |
| daughters | 1a | B | B | A | A |
| | 1b | A | B | A | A |
| | 1c | A | A | B | B |

The two alleles at each locus are designated A and B, respectively for the alleles present in Y24 and Y55. Each spore clone inherits an allele from one of its two parents, either the A allele from Y24 or the B allele from Y55. The alleles at these loci can be distinguished directly by testing for growth in specific media.

TABLE 2

Summary of the results of the Genome Mismatch Scanning test.

| Comparison # | Relative Pair | LOCUS | | | |
|---|---|---|---|---|---|
| | | CAN1 | URA3 | HIS4 | GAL2 |
| 1 | Y24/daughter 1a | − | − | + | + |
| 2 | Y55/daughter 1c | − | − | + | + |
| 3 | Y24/daughter 1c | + | + | − | − |
| 4 | Y55/daughter 1b | − | + | − | − |
| number of restriction fragments | | [4] | [4] | [3] | [5] |

"−" indicates no DNA was recovered for any of the restriction fragment bands detected by the DNA probe specific for the indicated locus (neglecting faint bands from cross-hybridization to unlinked sequences).
"+" indicates recovery of DNA in all restriction bands detected by the DNA probe specific to the indicated locus.
The number of restriction fragment bands surveyed by the probe used for the indicated locus is indicated in brackets in the bottom row of the table. The probes used in each case were bacteriophage lambda clones from the ordered collection established by Maynard Olsen. The specific clones used as probes were: CAN1: clone 5917, HIS4: clone 4711, URA3: clone 6150, GAL2: clone 6637. The clone numbers are the numbers assigned by Maynard Olsen. For convenience, only 4 of the eight possible parent daughter combinations were tested. The results of the genetic tests for 4 loci are shown in Table 1. Numerous other pairwise comparisons have subsequently been tested with similar results.

It is evident from the above results, that the subject methodology provides for numerous advantages. The methods provide access to a large set of highly polymorphic markers required for linkage mapping with small family units. A great increase in the effective number of informative markers is achieved without a corresponding increase in the number of individual tests, since all the markers are screened in parallel in a single procedure. By allowing much smaller sets of related individuals to be used for linkage mapping, the affected-relative-pair and homozygosity-by-descent mapping methods can greatly reduce the cost and labor involved in developing the human genetic map. Genomic mismatch scanning allows for the practical application of linkage mapping to genetically heterogeneous or quantitative traits, such as cardiovascular disease, asthma, psychiatric disorders, epilepsy, obesity, cancer and diabetes.

The subject methodology does not rely on any previously-mapped genetic markers. Thus, one can use the subject methodology to begin immediately to develop the genetic and physical maps of a genome for which little or no prior map information is available. This can find particularly important application in the breeding of plant or animal species, as well as in development of the genetics of such species.

Each pair-wise analysis allows sites of meiotic recombination to be mapped. In grandparent-grandchild pairs, identity-by-descent maps specifically identify the sites of meiotic recombination in the corresponding parent. Questions such as the relationship between the genetic and physical map, locations of sites of enhanced or diminished recombination, effects of age, sex and other factors on the frequency and distribution of meiotic recombination events, and the relationship between recombination and non-dysjunction can be readily investigated in this way.

Finally, the ability to detect directly regions of the genome that have lost heterozygosity may be useful in identifying putative tumor-suppressor genes and in the earlier diagnosis of malignancies, since loss of heterozygosity at specific loci appears to be an important genetic event in the development of many cancers.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for separating DNA duplexes capable of being used for genetic mapping or identification, from a complex mixture of DNA from two genetically related sources, wherein each of said sources contributes at least about $5 \times 10^4$ bp of DNA, said method comprising:

(a) isolating DNA from said two genetically related sources;

(b) digesting said DNA from said two sources to provide first restriction fragments;

(c) modifying the DNA from at least one of said sources by a method selected from the group consisting of: (i) methylation, (ii) use of a mixture of restriction enzymes in said digesting and (ii) incorporation of labeled nucleotides, wherein said modifying provides a means of distinguishing the DNA from said one source;

(d) denaturing said first restriction fragments to provide single stranded DNA;

(e) combining said single stranded DNA from said two sources to provide duplexes consisting of heterohybrids and homohybrids;

(f) separating homohybrids from heterohybrids;

(g) introducing nicks into heterohybrids having mismatches (h) introducing single stranded gaps in heterohybrids having nicks; and (i) separating gapped heterohybrids from ungapped heterohybrids;

wherein said separated DNA is useful for genetic identification or mapping.

2. A method according to claim 1, wherein the method of modifying the DNA from one of said sources is methylation and said separating of homohybrids from heterohybrids comprises the steps of:

digesting said duplexes with at least one methyl sensitive restriction enzyme to produce second restriction fragments under conditions wherein heterohybrids are not digested and the resulting termini of digested duplexes differ from those of said first restriction fragments;

wherein said introducing of single stranded gaps into DNA duplexes having nicks further introduces gaps at the termini of said second restriction fragments.

3. A method according to claim 1, wherein said introducing single stranded gaps further comprises:

incorporating labeled nucleotides into said single stranded gaps with DNA polymerase; and separating said labeled DNA from unlabeled DNA by means of said labeled nucleotides.

4. A method according to claim 1 wherein the method of modifying the DNA from one of said sources is use of a mixture of restriction enzymes, comprising the steps of:

digesting DNA from one of said sources with a restriction enzyme where the resulting termini have a 3' protruding end and digesting DNA from the other one of said sources with a restriction enzyme where the resulting termini have a 5' protruding end;

wherein the two protruding ends are complementary and on combining said single stranded DNA from said two sources to provide duplexes consisting of heterohybrids and homohybrids, only the heterohybrids will have termini with flush ends; and said separating of heterohybrids and homohybrids comprises the steps of:

ligating a oligonucleotide cap to said termini with flush ends;

introducing gaps into duplexes lacking a oligonucleotide cap; and isolating DNA duplexes lacking gaps.

5. A method for separating DNA fragments having genetic identity by descent from a complex mixture of DNA from two genetically related sources, wherein each of said sources contributes at least about $5 \times 10^4$ bp of DNA, said method comprising:

(a) isolating DNA from said two genetically related sources;

(b) digesting said DNA from said two sources to provide first restriction fragments;

(c) methylating the DNA from one of said sources with a sequence specific methylase;

(d) denaturing said first restriction fragments to provide single stranded DNA;

(e) combining said single stranded DNA from said two sources to provide duplexes consisting of heterohybrids and homohybrids;

(f) digesting said duplexes with at least one methyl sensitive restriction enzyme to produce second restriction fragments under conditions where only homohybrids are digested and the resulting termini of said second restriction fragments differ from those of said first restriction fragments;

(g) introducing nicks into mismatched DNA duplexes;

(h) introducing single stranded gaps into: (1) nicked DNA duplexes and (2) said second restriction fragments, to produce a mixture of single stranded, partially single stranded duplex and ungapped duplex DNA;

(i) isolating ungapped duplex DNA;

wherein said isolated ungapped DNA duplexes identify regions of genetic identity by descent between two related sources.

6. A method according to claim 5, wherein each of said genetically related sources contributes at least about $10^6$ bp of DNA.

7. A method according to claim 6, wherein said introducing of nicks into mismatched DNA duplexes is with the enzymes MutL, MutS and MutH of *E. coli*.

8. A method according to claim 6, wherein the enzyme exonuclease III of *E. coli* introduces said single stranded gaps into: (i) nicked DNA duplexes and (ii) said second restriction fragments.

9. A method according to claim 6, wherein said isolating of ungapped duplex DNA comprises the steps of:

combining said mixture of single stranded, partially single stranded duplex and ungapped duplex DNA with benzoylated naphthylated DEAE cellulose BNDO at high salt concentration, wherein single stranded and partially single stranded DNA binds to benzoylated naphthylated DEAE cellulose and separating bound DNA from unbound DNA to provide ungapped duplex DNA.

10. A method for separating and identifying DNA fragments having genetic identity from a complex mixture of DNA from two genetically related sources, wherein each of said sources contributes at least about $10^6$ bp of DNA, said method comprising:

(a) isolating DNA from said two genetically related sources;

(b) digesting said DNA from said two sources to provide first restriction fragments having termini with a 3' protruding end;

(c) methylating the DNA from one of said sources with a methylase specific for the sequence GATC;

(d) denaturing said restriction fragments to provide single stranded DNA;

(e) combining said single stranded DNA from said two sources to provide duplexes consisting of heterohybrids and homohybrids;

(f) digesting said duplexes with the restriction enzymes Mbo I and Dpn I to produce second restriction fragments wherein the resulting termini have 3' recessed or flush ends;

(g) introducing nicks into mismatched DNA duplexes with the enzymes MutL, MutS and MutH of *E. coli*;

(h) introducing single stranded gaps with exonuclease into: (i) nicked DNA duplexes and (ii) said second restriction fragments having 3' recessed or flush ends, to produce a mixture of single stranded, partially single stranded duplex and ungapped duplex DNA;

(i) combining said mixture of single stranded, partially single stranded duplex and ungapped duplex DNA with benzoylated naphthylated DEAE cellulose (BNDC) at high salt concentration, wherein single stranded and partially single stranded DNA binds to BNDC; and (j) separating bound DNA from unbound DNA to provide ungapped duplex DNA;

(k) labeling said ungapped duplex DNA for use as a probe; and identifying DNA fragments having genetic identity between two genetically related sources.

* * * * *